(12) United States Patent
Stinson

(10) Patent No.: US 7,574,799 B2
(45) Date of Patent: *Aug. 18, 2009

(54) METHODS OF MAKING MEDICAL DEVICES

(75) Inventor: Jonathan S. Stinson, Plymouth, MN (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 360 days.

This patent is subject to a terminal disclaimer.

(21) Appl. No.: 11/045,812

(22) Filed: Jan. 28, 2005

(65) Prior Publication Data

US 2005/0150096 A1    Jul. 14, 2005

Related U.S. Application Data

(63) Continuation of application No. 10/185,837, filed on Jun. 27, 2002, now Pat. No. 6,865,810.

(51) Int. Cl.
*B23P 25/00* (2006.01)
*A61F 2/06* (2006.01)

(52) U.S. Cl. .................. 29/896.6; 29/458; 29/527.2; 427/2.1; 427/2.24; 623/1.13; 623/1.46

(58) Field of Classification Search ........... 29/896.6, 29/458, 506, 516, 527.1, 527.2, 557; 623/1.13, 623/1.15, 1.16, 1.42, 1.44, 1.46, 901, 920; 427/2.1, 2.24; 72/367.1, 368
See application file for complete search history.

(56) References Cited

U.S. PATENT DOCUMENTS

| | | | | |
|---|---|---|---|---|
| 5,858,556 A | * | 1/1999 | Eckert et al. | 428/586 |
| 6,096,175 A | * | 8/2000 | Roth | 204/192.15 |
| 6,107,004 A | * | 8/2000 | Donadio, III | 430/320 |
| 6,312,463 B1 | * | 11/2001 | Rourke et al. | 623/1.39 |
| 6,344,055 B1 | * | 2/2002 | Shukov | 623/1.15 |
| 6,517,888 B1 | * | 2/2003 | Weber | 427/2.24 |
| 6,849,085 B2 | * | 2/2005 | Marton | 623/1.13 |
| 6,865,810 B2 | * | 3/2005 | Stinson | 29/896.6 |

* cited by examiner

*Primary Examiner*—Jermie E Cozart
(74) *Attorney, Agent, or Firm*—Fish & Richardson P.C.

(57) ABSTRACT

A method of making a stent includes providing a tubular member having a first layer, the first layer and the tubular member having different compositions, removing a portion of the tubular member, and removing a portion of the first layer from the tubular member.

59 Claims, 2 Drawing Sheets

METHODS OF MAKING MEDICAL DEVICES

CROSS-REFERENCE TO RELATED APPLICATION

This application is a continuation of and claims priority to U.S. application Ser. No. 10/185,837, filed Jun. 27, 2002 now U.S. Pat. No. 6,865,810 B2. The disclosures of these applications are incorporated by reference.

TECHNICAL FIELD

The invention relates to methods of making medical devices, such as, for example, endoprostheses.

BACKGROUND

The body includes various passageways such as arteries, other blood vessels, and other body lumens. These passageways sometimes become occluded or weakened. For example, the passageways can be occluded by a tumor, restricted by plaque, or weakened by an aneurysm. When this occurs, the passageway can be reopened or reinforced, or even replaced, with a medical endoprosthesis. An endoprosthesis is typically a tubular member that is placed in a lumen in the body. Examples of endoprosthesis include stents and covered stents, sometimes called "stent-grafts".

An endoprosthesis can be delivered inside the body by a catheter that supports the endoprosthesis in a compacted or reduced-size form as the endoprosthesis is transported to a desired site. Upon reaching the site, the endoprosthesis is expanded, for example, so that it can contact the walls of the lumen.

The expansion mechanism may include forcing the endoprosthesis to expand radially. For example, the expansion mechanism can include the catheter carrying a balloon, which carries the endoprosthesis. The balloon can be inflated to deform and to fix the expanded endoprosthesis at a predetermined position in contact with the lumen wall. The balloon can then be deflated, and the catheter removed.

In another delivery technique, the endoprosthesis is formed of an elastic material that can be reversibly compacted and expanded. During introduction into the body, the endoprosthesis is restrained in a compacted condition. Upon reaching the desired implantation site, the restraint is removed, for example, by retracting a restraining device such as an outer sheath, enabling the endoprosthesis to self-expand by its own internal elastic restoring force.

One method of making a stent includes laser cutting a tube of stent material to define the structure of the stent. Laser cutting, however, can form recast material, which is material from the tube that has melted, oxidized, and solidified on laser-cut surfaces. The recast material can make a stent more susceptible to failure (e.g., cracking or fracture) during manufacturing or in use. Accordingly, sometimes, the recast material is removed, e.g., by chemical milling and/or electropolishing, after laser cutting. To compensate for loss of material during the removal step(s), the metal tube can be made oversized, which can be wasteful and costly, particularly if the tube includes precious metals. The removal step(s) may also include using potent and/or hazardous chemicals.

SUMMARY

The invention relates to methods of making medical devices, such as, for example, endoprostheses.

The invention features a method of manufacturing an endoprosthesis, such as a stent, that includes using sacrificial material that covers one or more portions of a tube of stent material. During manufacturing, particularly during removal of recast material, the sacrificial material protects the stent material from material loss. As a result, although the tube of stent material can be formed oversized, the tube does not need to be formed oversized, thereby reducing the amount of stent material used. When the stent material includes precious materials, such as gold or platinum, reducing the amount of stent material reduces cost. The sacrificial material may also be capable of reacting with the stent material to form a product, such as an alloy, that is relatively easy to remove, e.g., compared to the pure stent material. As a result, less hazardous chemicals may be used during recast material removal.

In one aspect, the invention features a method of making a stent. The method includes providing a tubular member having a first layer, the first layer and the tubular member having different compositions, removing a portion of the tubular member, and removing a portion of the first layer from the tubular member.

In another aspect, the invention features a method of making a stent having struts including providing a tubular member having a first layer, the first layer and the tubular member having different compositions, removing a portion of the tubular member to form the struts and a portion of the first layer, and removing a portion of the first layer from the tubular member to provide the stent.

In another aspect, the invention features a method of making a stent including providing a member having a first layer, the first layer and the member having different compositions, removing a portion of the member to define an opening through the member, removing the first layer from the member, and forming the member into the stent. The member may have opposing edges, and the stent may be formed by connecting the edges. The stent can be formed by forming the member into a tube. The member can be tubular.

Embodiments of the aspects of the invention may include one or more of the following features. The tubular member and the first layer include metals. The method further includes finishing the tubular member into the stent, e.g., by electropolishing. A portion of the first layer is removed with the portion of the tubular member. The entire first layer is removed from the tubular member. An entire surface portion of the first layer is removed from the tubular member.

The first layer can be directly on the tubular member. The first layer can be on only a portion of the tubular member or on substantially an entire surface of the tubular member. The first layer can be on an inner surface and/or on an outer surface of the tubular member.

In some embodiments, the tubular member has a second layer, and the first and second layers are on opposing surfaces of the tubular member. The method may include removing a portion of the tubular member and the first and second layers, and removing the first and second layers from the tubular member.

The tubular member can be provided by co-drawing a first member that forms the tubular member and a second member that forms the first layer on an inner surface of the tubular member. The tubular member can be provided by co-drawing a first member that forms the tubular member and a second member that forms the first layer on an outer surface of the tubular member.

The method can include forming the first layer on the tubular member. The first layer may include a metal and may be formed by a process selected from a group consisting of electrodeposition and vapor deposition of the metal.

The stent may include struts, and the removing of the portion of the tubular member may include forming the struts.

The portion of the tubular member may be removed by a laser, by dissolving the first layer, by melting the first layer, and/or by mechanically removing the first layer.

The tubular member may include a material selected from a group consisting of platinum, gold, palladium, rhenium, tantalum, tungsten, molybdenum, rhenium, nickel, cobalt, stainless steel, Nitinol, and alloys thereof. The first layer may include a material selected from a group consisting of steel, cadmium, lead, magnesium, tin, zinc, titanium, stainless steel, and aluminum.

The method may include forming a drug-releasing layer on the stent.

In another aspect, the invention features a stent, made according to the methods described herein.

Other aspects, features, and advantages of the invention will be apparent from the description of the preferred embodiments thereof and from the claims.

DETAILED DESCRIPTION

Figure 1:
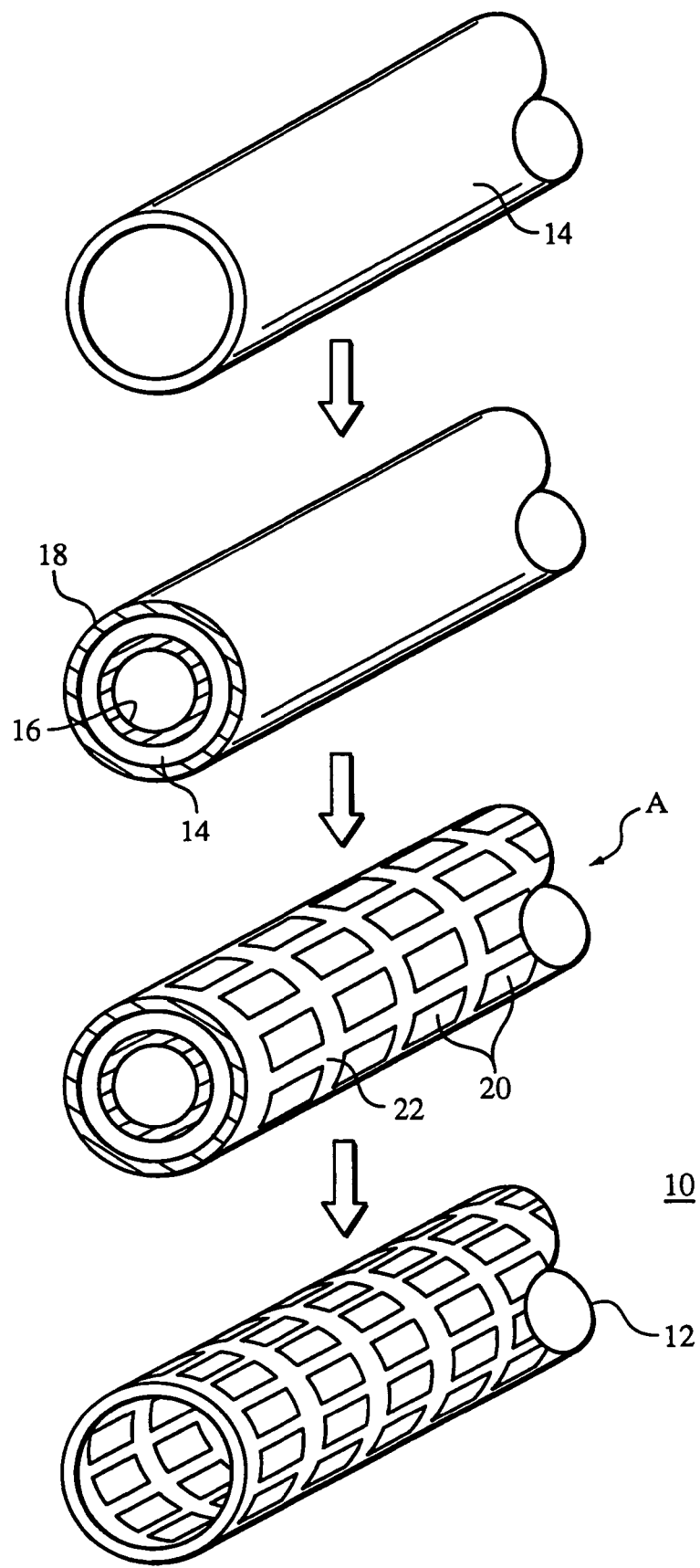
FIG. 1 is a schematic diagram of a method of making a stent.

Referring to FIG. 1, a method 10 of making a stent 12 is shown. Method 10 generally includes providing a tubular member 14 that ultimately becomes stent 12, and forming an inner layer 16 and an outer layer 18 on the tubular member. Tubular member 14 is made of a stent material, e.g., platinum, and layers 16 and 18 can be made of, e.g., carbon steel. Portions of tubular member 14 and layers 16 and 18 are then removed, e.g., by laser cutting, to form openings 20 and struts 22 of stent 12. Subsequently, layers 16 and 18 are removed from tubular member 14 to yield stent 12.

Layers 16 and 18 serve as sacrificial layers that are ultimately removed at the end of method 10. Here, rather than starting with an oversized tubular member to compensate for loss of material that may occur during removal of recast material, a relatively smaller tubular member 14 can be used with layers 16 and 18. For example, tubular member 14 and layers 16 and 18 can have a total dimension similar to that of an oversized tubular member. During removal of recast material, layers 16 and 18 are sacrificed, reducing the amount of tubular member 14 that is affected by recast material removal. In embodiments in which tubular member 14 includes precious metals, such as platinum, using layers 16 and 18 can reduce cost and waste. In other embodiments, an oversized tubular member can be used.

Furthermore, without wishing to be bound by theory, it is believed that during laser cutting, portions of layers 16 and 18 can pave cut surfaces of tubular member 14 and/or react with the tubular member, e.g., at the cut surfaces to form products such as alloys. Some reaction products can be more easily removed, e.g., by chemical etching, than a pure stent material, such as an acid-resistant precious metal. As a result, in some embodiments, less hazardous materials may be used in the post-laser cutting removal step(s). Some reaction products may also protect the cut surfaces by making the surfaces less susceptible to oxidation.

Moreover, since tubular member 14 can be relatively small, smaller ingots can be used to form the tubular member. Smaller ingots can be formed with relatively high yield rates, i.e., low waste, and relatively high quality control. Also, during manufacturing, layers 16 and 18 can protect tubular member 14, e.g., by lowering the oxidation of the tubular member by the environment and/or by reducing contamination of the tubular member, e.g., from machining equipment. Consequently, manufacturing steps, such as annealing to enhance the physical properties to tubular member 14, e.g., ductility, may be performed without certain handling equipment, such as vacuum or inert gas annealing chambers, which can further reduce cost and inconvenience.

Tubular member 14 can be made of any material that can be used in a stent. The material is preferably biocompatible. Examples of stent materials include noble metals, such as platinum, gold, and palladium, refractory metals, such as tantalum, tungsten, molybdenum and rhenium, and alloys thereof. Other examples of stent materials include stainless steels, stainless steels alloyed with noble and/or refractory metals, nickel-based alloys (e.g., those that contained Pt, Au, and/or Ta), iron-based alloys (e.g., those that contained Pt, Au, and/or Ta), cobalt-based alloys (e.g., those that contained Pt, Au, and/or Ta), and Nitinol. Tubular member 14 can be made, for example, by extrusion and drawing, or by boring a solid billet of stent material. As an example, tubular member 14 can be made from a casted two-inch diameter ingot that is rough machined, rolled, forged, and/or extruded to a 1.5-inch diameter by six-inch long billet. A one-inch diameter bore can be formed in the billet by upset forging and/or electrical discharge machining (EDM). As described below, tubular member 14 can have dimensions that are near final stent size or greater.

Tubular member 14 can be annealed after it is formed. In general, annealing can be performed after any step (such as forging, extrusion, or drawing) that has reduced the formability (e.g., ductility) of tubular member 14. Annealing tubular member 14 can increase the formability of the tubular member to a level sufficient for further processing (e.g., without the tubular member cracking or fracturing).

Layers 16 and 18 can include any material that can be formed on tubular member 14 and subsequently removed. Examples of materials for layers 16 and 18 are those that are relatively convenient to handle, relatively convenient to form on tubular member 14, relatively easy to remove, e.g., chemically, and/or relatively inexpensive. Preferably, the materials for layers 16 and 18 can react with the stent material to form a product that is convenient or easy to remove. Layers 16 and 18 can have similar melting points as that of tubular member 14 or higher, e.g., so that the layers can be annealed with the tubular member, i.e., the layers do not melt or degrade during heating. In some embodiments, materials for layers 16 and 18 have relatively low melting points, e.g., so that the layers can be removed by heating. Examples of materials for layers 16 and 18 include metallic materials, such as carbon steel, cadmium, lead, magnesium, tin, zinc, titanium, stainless steel (e.g., 304L or 316L stainless steel), and aluminum. The thickness of each layer 16 or 18 can be about 0.25-2 times, e.g., 0.5-1 time, the wall thickness of tubular member 14. Layers 16 and 18 can have the same or different compositions.

Numerous methods can be used to form layers 16 and 18 on tubular member 14. For example, a tubular member 14 that is larger than final stent size can be sandwiched between layers 16 and 18 by placing a tight fitting tube (e.g., a steel tube) around the tubular member, and another tight fitting tube (e.g., a hollow or solid die or a mandrel) in the tubular member. Tubular member 14 and the sandwiching tubes can then be co-drawn, e.g., until the tubular member is near final stent size. As an example, a 1.5-inch diameter tubular member having a one-inch diameter bore can be placed into an outer steel tube having a 1.5193-inch O.D. and a 1.5-inch I.D. An inner steel tube having a one-inch O.D. and a 0.9745-inch I.D. can be placed in the tubular member. The tubular member and sandwiching steel tubes can be drawn until the O.D. and the I.D. of the tubular member are reduced to about 0.07 and 0.06 inch, respectively. A 0.0002-inch thick steel layer can be on each surface of the tubular member after drawing.

In other embodiments, tubular member 14 can be formed, e.g., drawn, to near final stent size, and layers 16 and 18 are subsequently formed on the tubular member. Methods of forming layers 16 and 18 include, for example, electrodeposition, spraying, e.g., plasma spraying, dipping in molten material, e.g., galvanizing, chemical vapor deposition, and physical vapor deposition.

After layers 16 and 18 are formed on tubular member 14, portions of the layers and tubular member are removed to form the structure (e.g., openings 20 and struts 22) of stent 12. The portions can be removed by laser cutting, as described in U.S. Pat. No. 5,780,807, hereby incorporated by reference in its entirety. In certain embodiments, during laser cutting, a liquid carrier, such as a solvent or an oil, is flowed through tubular member 14 (arrow A). The carrier can prevent dross formed on one portion of tubular member 14 from re-depositing on another portion, and/or reduce formation of recast material on the tubular member. Other methods of removing portions of tubular member 14 and layers 16 and 18 can be used, such as mechanical machining (e.g., micro-machining), electrical discharge machining (EDM), and photoetching (e.g., acid photoetching).

After the structure of stent 12 is formed, layers 16 and 18 are removed to yield stent 12. Layers 16 and 18 can be dissolved, e.g., by immersion in an acid such as nitric acid, which can also remove certain recast material formed on tubular member 14 (now formed into stent 12). Alternatively or in addition, layers 16 and 18 can be mechanically removed, e.g., by grinding, melting, e.g., for layers having sufficiently low melting points, and/or subliming.

Stent 12 can then be finished, e.g., electropolished to a smooth finish, according to conventional methods. As an example, about 0.0001 inch of the stent material can be removed from each surface by chemical milling and electropolishing to yield a stent having a 0.0695-inch O.D. and a 0.0605-inch I.D. Stent 12 can then be annealed.

Stent 12 can be used, e.g., delivered and expanded, according to conventional methods.

Generally, stent 12 can be a conventional stent, e.g., balloon expandable, self-expandable, or a combination of both. Stent 12 can also be a part of a stent-graft. The stent-graft can be a stent attached to a biocompatible, non-porous or semi-porous polymer matrix made of polytetrafluoroethylene (PTFE), expanded PTFE, polyethylene, urethane, or polypropylene. Stent 12 can include a releasable therapeutic agent or a pharmaceutically active compound, such as described in U.S. Pat. No. 5,674,242, and commonly-assigned U.S. Ser. No. 09/895,415, filed Jul. 2, 2001, all hereby incorporated by reference. The therapeutic agents or pharmaceutically active compounds can include, for example, anti-thrombogenic agents, antioxidants, anti-inflammatory agents, anesthetic agents, anti-coagulants, and antibiotics. Examples of stent 12 are described in U.S. Pat. Nos. 5,725,570 and 5,234,457, all hereby incorporated by reference.

OTHER EMBODIMENTS

Figure 2:
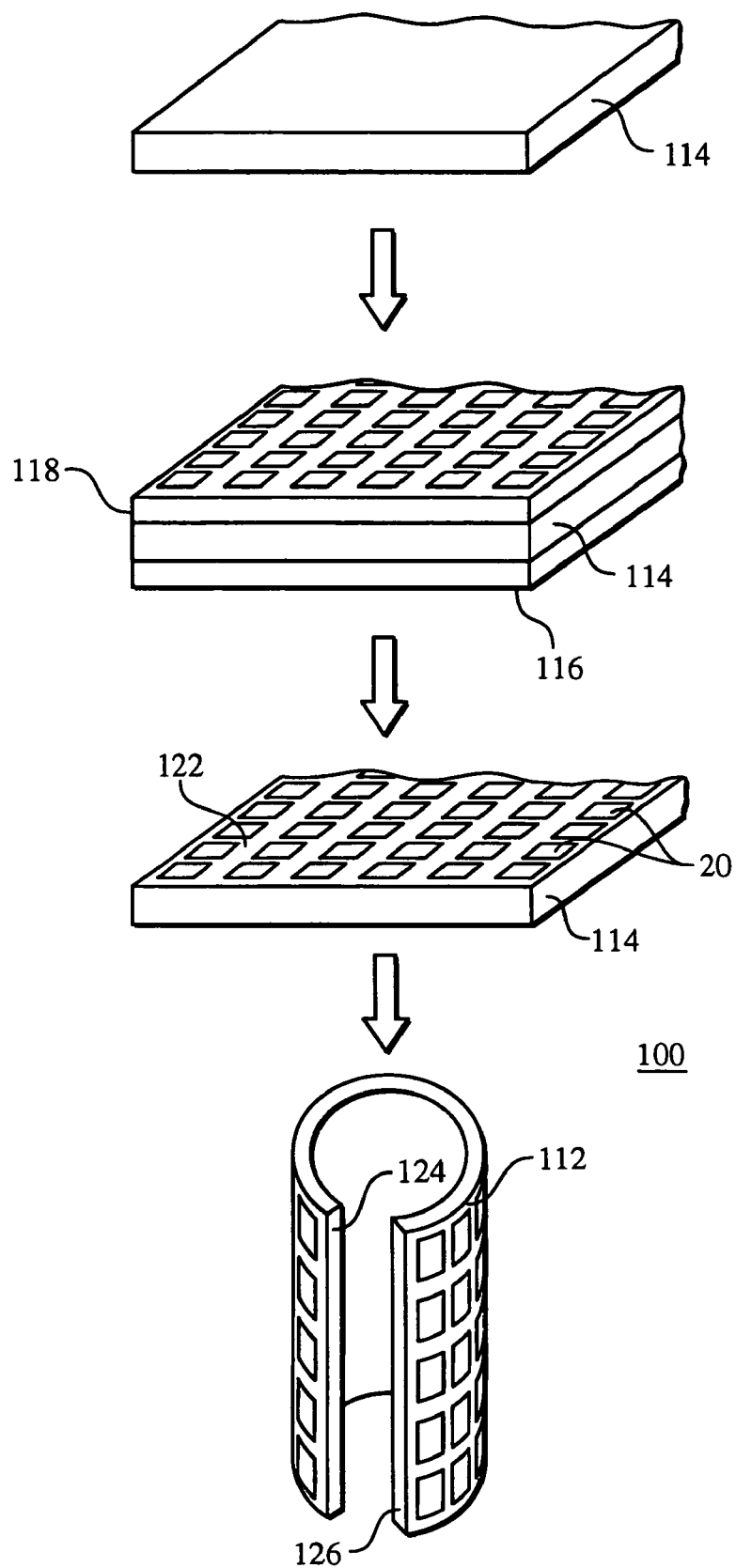
FIG. 2 is a schematic diagram of a method of making a stent.

In other embodiments, a non-tubular member can be initially used to form a stent. Referring to FIG. 2, a method 100 of forming a stent 112 begins with using a non-tubular member 114 (here, a sheet). Member 114 can be similar in composition to tubular member 14 described above. Member 114 can be formed, for example, by forging, rolling, and/or extrusion. Next, sacrificial layers 116 and 118, which are similar to layers 16 and 18, are formed on member 114, as generally described above. Portions of member 114 and layers 116 and 118 are then removed, e.g., by laser cutting, to form openings 120 and struts 112 of stent 112. Layers 116 and 118 are then removed, e.g., by chemical etching, to leave member 114. Member 114 can be formed into stent 112 by connecting opposing edges 124 and 126, e.g., by welding. Stent 112 can be finished as described above. In some embodiments, opposing edges of member 114 and layers 116 and 118 can be connected together to form a tube prior to laser cutting.

As an example, a casted and rough machined two-inch diameter by six inch long ingot of stent material can be upset forged and extruded down to a bar about one inch thick by one inch wide by 18.85 inch long for plate and strip rolling. The bar can be placed within a tight fitting steel container with a wall thickness of 0.0435 inch. The steel-covered bar can be subjected to plate and strip rolling operations until the thickness of the stent material is 0.0046 inch and the total sandwich thickness is 0.0050 inch. A 0.0002-inch thick steel layer may be on each surface of the stent material. A stent tubing can be formed by rolling and laser welding of the steel-sandwiched stent material. The welded tubing can be laser machined to form the structure of the stent, and the machined stent can be immersed in a nitric acid solution to dissolve the steel from the surfaces of the stent and the recast material on the cut surfaces. The stent can then be electropolished to a smooth surface finish, with 0.00005 inch of stent material removed from each surface from chemical milling and electropolishing.

In some embodiments, one or more of sacrificial layers 16, 18, 116, or 118 cover selected portions of member 14 or 114. For example, the sacrificial layers may cover only portions of member 14 or 114 that become the struts of the stent, i.e., portions of the member 14 or 114 that are removed to form the openings of the stent are not covered by the sacrificial layers. Selective coverage of members 14 or 114 can be performed, e.g., by masking techniques.

In certain embodiments, layers 16, 18, 116, or 118 are formed on the stent material ingot to protect the stent material during billet or tube forming. The melting points of layers 16, 18, 116, or 118 may be about 50% of the melting point of stent material or more.

In other embodiments, only one layer (e.g., layer 16, 18, 116, or 118) is formed on the member (e.g., member 14 or 114) that ultimately becomes the stent. As an example, a two-inch diameter ingot of stent material can be rough machined, rolled, forged, and/or extruded down to a 1.5-inch diameter by six-inch long billet. A one-inch diameter hole can be made in the billet by upset forging or electrical discharge machining. The billet can be placed inside a tight fitting steel tube with a 1.5-inch diameter I.D. and a wall thickness of 0.0045 inch. The steel covered billet can be subjected to tube drawing operations until the O.D. and I.D. are 0.0700 inch and 0.0602 inch, respectively. A 0.0001-inch thick steel layer may remain on the outer surface of the stent material tubing. Laser cutting of the stent struts can be performed. The machined tube can be immersed in a nitric acid solution to dissolve the steel from the outer surface of the tube and the steel recast material on the cut surfaces. The stent can then be chemical milled and electropolished to a smooth surface finish (e.g., 0.0003 inch of stent material removed from each surface). The finished stent dimensions can be 0.0695 inch O.D. and 0.0605 inch I.D.

In some embodiments, layers 16, 18, 116 and/or 118 are not completely removed from tubular member 14 or member 114 because, for example, the layer(s) can enhance the function or performance of the stent. For example, a thin film of titanium or 316 L stainless steel may remain on member 14 or 114 to enhance biocompatibility of a gold or tungsten member 14 or 114. An entire surface portion of layers 16, 18, 116 and/or 118 can be removed, leaving the layers reduced in thickness but still remaining on member 14 or 114.

More than one sacrificial layer can be formed on each side of member 14 or 114. A sacrificial layer may be in direct contact with member 14 or 114, or there may be intermediate layers between the sacrificial layer and member 14 or 114.

Other embodiments are within the claims.

What is claimed is:

1. A method of making a stent, the method comprising:
    providing a tubular member having a first layer, the first layer and the tubular member having different metallic compositions and having a first thickness;
    removing a portion of the tubular member; and
    removing a portion of the first layer from the tubular member, wherein the tubular member and the first layer have a reduced second thickness.
2. The method of claim 1, wherein the tubular member and the first layer comprise metals.
3. The method of claim 1, further comprising finishing the tubular member into the stent.
4. The method of claim 3, wherein the tubular member is finished by electropolishing.
5. The method of claim 1, wherein the first layer is directly on the tubular member.
6. The method of claim 1, wherein the first layer is on only a portion of the tubular member.
7. The method of claim 1, wherein the first layer is on substantially an entire surface of the tubular member.
8. The method of claim 1, wherein the first layer is on an inner surface of the tubular member.
9. The method of claim 1, wherein the first layer is on an outer surface of the tubular member.
10. The method of claim 1, wherein a portion of the first layer is removed with the portion of the tubular member.
11. The method of claim 1, wherein the tubular member has a second layer, the first and second layers being on opposing surfaces of the tubular member, and the method comprises removing a portion of the tubular member and the first and second layers, and removing the first and second layers from the tubular member.
12. The method of claim 1, wherein the tubular member is provided by co-drawing a first member that forms the tubular member and a second member that forms the first layer on an inner surface of the tubular member.
13. The method of claim 1, wherein the tubular member is provided by co-drawing a first member that forms the tubular member and a second member that forms the first layer on an outer surface of the tubular member.
14. The method of claim 1, further comprising forming the first layer on the tubular member.
15. The method of claim 14, wherein the first layer comprises a metal and is formed by a process selected from a group consisting of electrodeposition and vapor deposition of the metal.
16. The method of claim 1, wherein the stent comprises struts, and the removing of the portion of the tubular member comprises forming the struts.
17. The method of claim 1, wherein the portion of the tubular member is removed by a laser.
18. The method of claim 1, wherein the first layer is removed by dissolving the first layer.
19. The method of claim 1, wherein the first layer is removed by melting the first layer.
20. The method of claim 1, wherein the first layer is removed by mechanically removing the first layer.
21. The method of claim 1, wherein the tubular member comprises a material selected from a group consisting of platinum, gold, palladium, rhenium, tantalum, tungsten, molybdenum, rhenium, nickel, cobalt, stainless steel, Nitinol, and alloys thereof.
22. The method of claim 1, wherein the tubular member comprises a material selected from a group consisting of platinum, gold, and tantalum.
23. The method of claim 1, wherein the first layer comprises a material selected from a group consisting of steel, cadmium, lead, magnesium, tin, zinc, titanium, stainless steel, and aluminum.
24. The method of claim 1, wherein the first layer comprises a steel.
25. The method of claim 1, further comprising forming a drug-releasing layer on the stent.
26. The method of claim 1, wherein the entire first layer is removed from the tubular member.
27. The method of claim 1, wherein an entire surface portion of the first layer is removed from the tubular member.
28. A method of making a stent, the method comprising:
    providing a member having a first layer, the first layer and the member having different metallic compositions and having a first thickness;
    removing a portion of the member to define an opening through the member;
    removing a portion of the first layer from the member, wherein the member and the first layer have a reduced second thickness; and
    forming the member into the stent.
29. The method of claim 28, wherein the member has opposing edges, and the stent is formed by connecting the edges.
30. The method of claim 28, wherein the stent is formed by forming the member into a tube.
31. The method of claim 28, wherein the member is tubular.
32. The method of claim 28, wherein the member and the first layer comprise metals.
33. The method of claim 28, further comprising finishing the member into the stent.
34. The method of claim 33, wherein the tubular member is finished by electropolishing.
35. The method of claim 28, wherein the first layer is directly on the member.
36. The method of claim 28, wherein the first layer is on only a portion of the member.
37. The method of claim 28, wherein the first layer is on substantially an entire surface of the member.
38. The method of claim 28, wherein a portion of the first layer is removed with the portion of the member.
39. The method of claim 28, wherein the member has a second layer, the first and second layers being on opposing surfaces of the member, and the method comprises removing a portion of the member and the first and second layers, and removing the first and second layers from the member.
40. The method of claim 28, further comprising forming the first layer on the member.
41. The method of claim 40, wherein the first layer comprises a metal and is formed by a process selected from a group consisting of electrodeposition and vapor deposition of the metal.

42. The method of claim 28, wherein the stent comprises struts, and the removing of the portion of the member comprises forming the struts.

43. The method of claim 28, wherein the portion of the member is removed by a laser.

44. The method of claim 28, wherein the first layer is removed by dissolving the first layer.

45. The method of claim 28, wherein the first layer is removed by melting the first layer.

46. The method of claim 28, wherein the first layer is removed by mechanically removing the first layer.

47. The method of claim 28, wherein the member comprises a material selected from a group consisting of platinum, gold, palladium, rhenium, tantalum, tungsten, molybdenum, rhenium, nickel, cobalt, stainless steel, Nitinol, and alloys thereof.

48. The method of claim 28, wherein the member comprises a material selected from a group consisting of platinum, gold, and tantalum.

49. The method of claim 28, wherein the first layer comprises a material selected from a group consisting of steel, cadmium, lead, magnesium, tin, zinc, and aluminum.

50. The method of claim 28, wherein the first layer comprises a steel.

51. The method of claim 28, further comprising forming a drug-releasing layer on the stent.

52. The method of claim 28, wherein the entire first layer is removed from the member.

53. The method of claim 28, wherein an entire surface portion of the first layer is removed from the member.

54. A method of making a stent having struts, the method comprising:
 providing a tubular member having a first layer, the first layer and the tubular member having different metallic compositions and having a first thickness;
 removing a portion of the tubular member to form the struts and a portion of the first layer; and
 removing the first layer from the tubular member to provide the stent, wherein the tubular member has a second thickness.

55. The method of claim 54, wherein the first layer is on an inner surface of the tubular member.

56. The method of claim 54, wherein the first layer is on an outer surface of the tubular member.

57. The method of claim 54, wherein the tubular member comprises a second layer on the tubular member, the first and second layers being on opposing surfaces of the tubular member.

58. The method of claim 54, wherein the first layer is on an entire surface of the tubular member.

59. The method of claim 54, further comprising forming a drug-releasing layer on the stent.

\* \* \* \* \*